United States Patent [19]
Whiting et al.

[11] Patent Number: 5,738,213
[45] Date of Patent: Apr. 14, 1998

[54] GUIDEWIRE HOLDER WITH EASY GUIDEWIRE ACCESS

[75] Inventors: John Whiting, Salt Lake City; Brian W. Stevens, Pleasant Grove; William Padilla, Sandy; Garlyn W. Hendry, Salt Lake City; Fred P. Lampropoulos, Sandy, all of Utah

[73] Assignee: Merit Medical Systems, Inc., South Jordan, Utah

[21] Appl. No.: 620,267

[22] Filed: Mar. 22, 1996

[51] Int. Cl.$^6$ .............................. B65D 83/10; A61B 5/00
[52] U.S. Cl. .......................... 206/364; 128/772; 206/210; 206/438; 604/171
[58] Field of Search .................. 604/171; 128/772; 206/369, 363, 409, 438, 210

[56] References Cited

U.S. PATENT DOCUMENTS

| | | | |
|---|---|---|---|
| 1,971,570 | 8/1934 | Lukens | 206/210 |
| 2,585,312 | 2/1952 | Harkness et al. | 206/210 |
| 3,100,487 | 8/1963 | Bathish | 206/364 X |
| 3,683,928 | 8/1972 | Kuntz | 206/364 X |
| 3,854,479 | 12/1974 | Duke | 206/364 X |
| 4,139,096 | 2/1979 | Sieger | |
| 4,721,123 | 1/1988 | Cosentino et al. | 604/171 X |
| 4,869,367 | 9/1989 | Kawasaki et al. | |
| 4,903,826 | 2/1990 | Pearce | 206/409 X |
| 4,936,448 | 6/1990 | Holloway | 206/364 |
| 5,105,943 | 4/1992 | Lesko et al. | |
| 5,125,416 | 6/1992 | Phillips | |
| 5,279,573 | 1/1994 | Klosterman | |
| 5,392,918 | 2/1995 | Harrison | |
| 5,611,428 | 3/1997 | Banerian | 206/364 |

*Primary Examiner*—Bryon P. Gehman
*Attorney, Agent, or Firm*—Workman, Nydegger & Seeley

[57] ABSTRACT

Guidewire holders to store one or more coiled guidewires substantially immersed in a storage fluid are provided. Some embodiments are more suited to storing a single guidewire holder while other embodiments are designed specifically to hold a plurality of guidewires. The guidewire holder is generally configured as a shallow pan in a circular or ovoid shape with a periphery to hold the coiled guidewires. At least a portion of the guidewire holder is shaped so that the coiled guidewire is held away from at least the outer periphery of the holder. This enables a healthcare professional to reach into the guidewire holder and grasp a portion of the guidewire in order to easily extract the coiled guidewire from the holder.

17 Claims, 7 Drawing Sheets

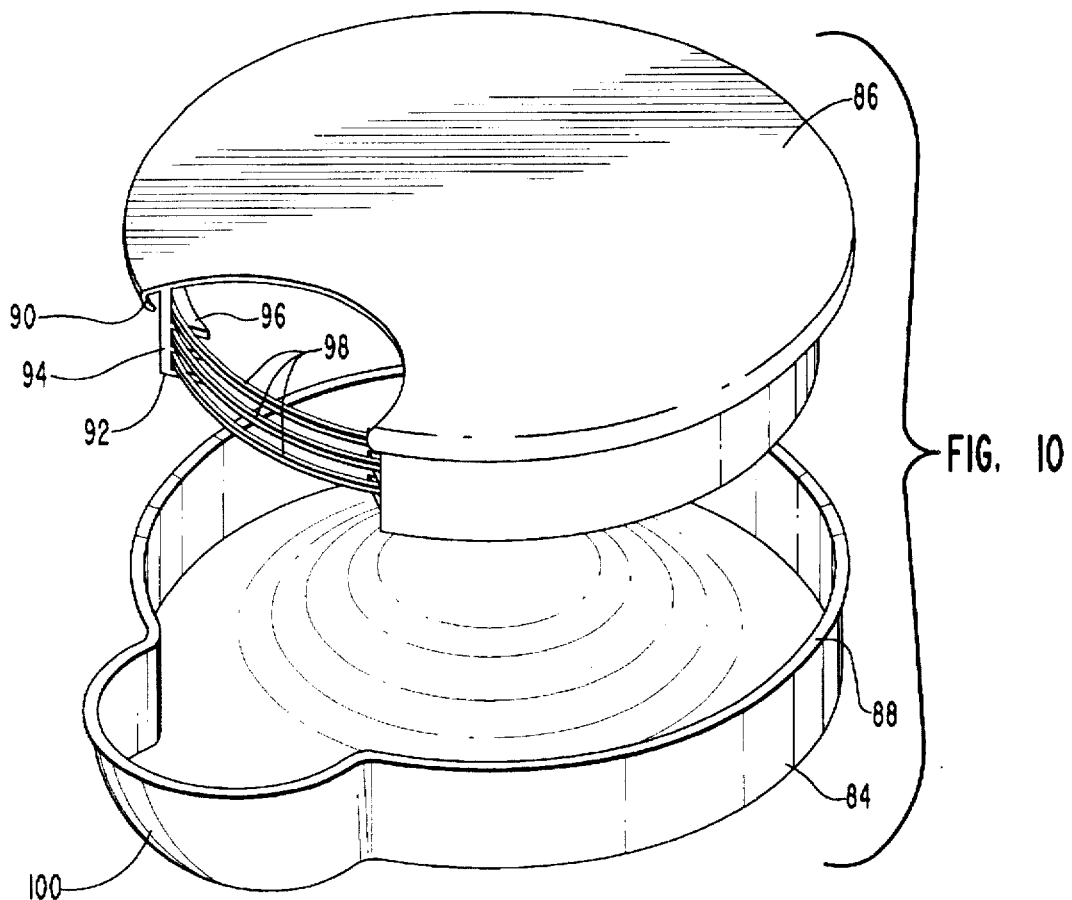
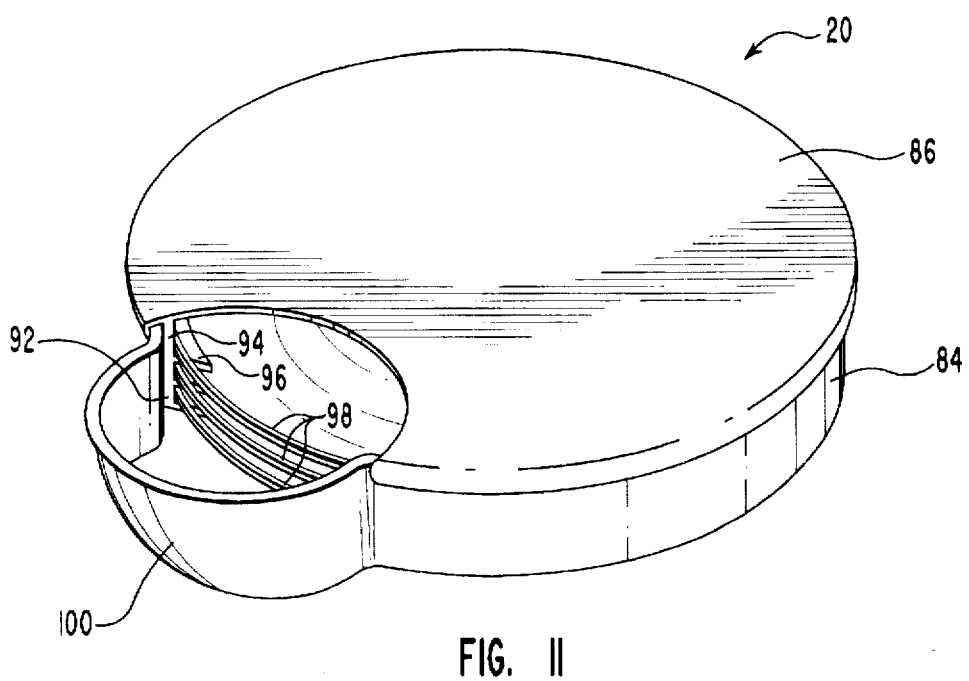

GUIDEWIRE HOLDER WITH EASY GUIDEWIRE ACCESS

BACKGROUND OF THE INVENTION

1. The Field of the Invention

This invention relates to containers for storage and retrieval of coiled wires and, more particularly, to containers for storage and retrieval of coiled medical guidewires used in a variety of surgical procedures.

2. Present State of the Art

Many modern medical procedures require the use of medical guidewires. Medical guidewires have a variety of structural features and configurations depending on the particular medical procedure with which they are to be used. Generally speaking, however, guidewires are used in medical procedures to direct a catheter to an identified location or site within a patient's cardiovascular or peripheral vascular system for the purpose of diagnosis or treatment. Typically, the guidewire is placed percutaneously into a patient's blood vessel and directed to the previously identified site. A catheter is then advanced over the guidewire until the functional structure of the catheter is located in proximity to the previously identified site. The catheter is then utilized to accomplish the selected medical procedure. Depending on the medical procedure to be accomplished and the particular structure of the catheter, the guidewire may be withdrawn from the vascular system before, during, or after utilization of the catheter.

A typical example of the above process would be utilization of a guidewire to direct an anglographic catheter to the site of a vascular obstruction. Thereafter an angioplasty catheter, such as a balloon angioplasty catheter, may be advanced over the guidewire to the site of the obstruction. The balloon is then inflated to reduce or eliminate the vascular obstruction. Other catheters are designed to perform different procedures such as application of ultrasound to an obstruction, delivery of drugs, execution of diagnostic procedures, or other application of drugs, energy, or other forces to a particular location within the body.

The procedures utilizing guidewires typically require that the guidewire employed be of a precise diameter or other specific construction. Additionally, several different guidewires can be required for a single medical procedure. This creates the need to store one or more guidewires in a manner which allows access to various guidewires throughout the medical procedure.

In order to prepare guidewires for use during a medical procedure, the guidewires are typically removed from any associated packaging and transport containers, and placed into an open tray which is typically filled with a storage fluid, such as a heparin solution. When the guidewire is needed during the medical procedure, a healthcare professional will reach into the tray, grasp the appropriate guidewire, and remove it from the storage solution.

Such a storage system, however, often creates many problems. For example, if multiple guidewires are to be utilized during a medical procedure, it can be difficult to identify the appropriate guidewire if they are placed within the same open storage tray. If multiple trays are used, they can take up a significant amount of space. Additionally, guidewires used in many medical applications are fine, with diameter ranging from 0.011 inches to 0.030 inches and because of the surgical gloves worn by healthcare professionals during a medical procedure, removing the guidewires from an open tray can be very difficult.

Guidewires used in medical procedures are often several feet in length. In order to store the long guidewires effectively, they are typically coiled before being placed in the storage tray. Because of the resiliency of the materials used to form the guidewires, the guidewires generally expand until they rest along the outside edge or rim of the storage tray. This can make it difficult to grasp the guidewire to remove it from the tray. When a healthcare professional reaches into the storage tray to retrieve a guidewire, the surgical gloves which are worn often make it difficult to grasp a portion of the guidewire in order to remove the guidewire from the storage tray. When multiple guidewires are placed within a single storage tray, they all tend to expand so as to rest along the outside edge or rim of the storage tray and thus create even more problems for a healthcare professional in trying to identify and remove a particular guide wire.

Another problem associated with open storage trays is retaining the guidewires immersed in the storage fluid. Once guidewires are coiled and placed into the storage tray, they generally spring open and to rest among the outside edge or rim of the storage tray. Some storage trays in the prior art have sidewalls that slope slightly outward (e.g., the angle formed between the sidewalls and the bottom of the storage tray is somewhat greater than 90°). If the storage tray is jostled, the guidewire can work its way up the sides of the tray and spring open and out of the pan.

Some guidewires are coated with a hydrophilic coating in order to make the process of passing a guidewire through a body vessel and passing a catheter over the guidewire easier. These coatings tend to make the guidewire "slippery." When such a guidewire is required, it can often be very difficult to grasp a portion of the guidewire while wearing surgical gloves in order to remove it from the storage tray. This is particularly true where the guidewire has sprung open so as to rest firmly against the sides of the storage tray. Open storage trays also allow the storage fluid to be easily spilled during a medical procedure.

In order to overcome some of the problems associated with storing guidewires, one guidewire holder has been developed which is formed from a coiled tube. The end of the coiled tube is bent into a vertical position and flared. The tube is filled with a storage fluid. Guidewires are then fed through the opening and around the coils so as to be submersed in the storage fluid.

Unfortunately, such a guidewire storage unit also creates additional problems. For instance, because of the relatively small diameter of the coiled tube, a portion of the end of the guidewire must extend out of the coiled tube so a healthcare professional can grasp the end of the guidewire and remove it from the storage unit. Thus, this type of storage unit requires that a portion of the guidewire be exposed to the atmosphere instead of residing underneath a storage fluid. Such an arrangement increases the likelihood of contamination of the guidewire before use.

SUMMARY AND OBJECTS OF THE INVENTION

The present invention has been developed in response to the current state of the art and, in particular, to the need for a guidewire holder which is capable of holding one or more guidewires immersed in a storage fluid while simultaneously providing easy access to the guidewires. It is, therefore, an object of the present invention to provide a guidewire holder which retains one or more coiled guidewires substantially immersed in a storage fluid.

It is another object of the present invention to provide a guidewire holder which allows easy removal of the guidewires stored therein.

It is a further object of the present invention to provide a guidewire holder which reduces the amount of storage fluid required to store one or more guidewires substantially immersed in the storage fluid.

It is yet another object of the present invention to provide a guidewire holder which retains the guidewires stored therein in a manner which reduces the likelihood that the guidewires will escape the holder due to the resiliency of the guidewires.

A still further object of the present invention is to provide a guidewire holder which reduces the likelihood that storage fluid will be spilled if the guidewire holder is accidentally jostled during a medical procedure.

Additional objects and advantages of the invention will be set forth in the description which follows, and in part will be obvious from the description, or maybe learned by the practice of the invention. The objects and advantages of the invention maybe realized and obtained by means of the instruments and combinations particularly pointed out in the appended claims.

Briefly summarized, the invention comprises various embodiments which are capable of storing one or more coiled guidewires in a storage fluid, yet provide easy removal of individual guidewires. The guidewire holder is generally configured as a shallow pan in a circular or ovoid shape with a periphery to hold a coiled guidewire. At least a portion of the guidewire holder is shaped so that the coiled guidewire is suspended and does not contact the holder and provides access to a portion of the coiled guidewire. This enables a healthcare professional to reach into the guidewire holder and grasp a portion of guidewire in order to easily extract the coiled guidewire from the holder. The guidewire holder is typically filled with a storage solution so the guidewires are substantially immersed in the storage fluid.

In one embodiment, the guidewire holder comprises a shallow pan area with sidewalls canted slightly inward. As the coiled guidewire springs open against the sides of the pan, the canted sides force the guidewire into the storage fluid contained therein. The guidewire holder has formed thereon an access portion which suspends a portion of the guidewire coils so the coiled guidewires do not contact the inside surface of the pan. The guidewire coils can thus be grasped and the guidewire can easily be removed from the pan. A cover portion is included which has an opening to allow insertion and removal of a coiled guidewire. The opening in the cover coincides with the access portion of the guidewire holder. The embodiment can also include a domed bottom to reduce the amount of storage fluid needed to cover the guidewires contained in the holder. Such a domed bottom will tend to channel the storage fluid to the outer periphery of the guidewire holder where the coiled guidewires reside. Finally, interlocking portions allow multiple guidewire holders to be stacked in order to reduce the amount of space they take up.

In a second embodiment, inward canted sides are replaced by a series of canted ribs attached to the cover. The ribs extend down the sides of the pan and have a cant so as to force a coiled guidewire down into the storage fluid. In this embodiment, the pan portion of the guidewire holder can have vertical or slightly outward canting sides. Such an arrangement facilitates injection molding of the device.

In yet another embodiment, the ribs are formed with individual shelf structures which are designed to retain individually coiled guidewires. In this way, a plurality of guidewires can be contained within the same pan and yet provide ease of access due to the vertical and horizontal separation between the guidewires.

In yet another embodiment, coiled guidewires are placed within shelf structures formed within the lid. The shelf structures are designed to separate the guidewires vertically and suspend a portion of the guidewire coils away from any surface to allow the guidewires to be easily grasped. The lid is then attached to the shallow park area to immerse the coiled guidewires in a storage fluid.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawing depict only typical embodiments of the invention and are not therefore to be considered to be limiting of its scope, the invention will be described and explained with additional specificity and detail through the use of the accompanying drawings in which:

FIG. 10 is an exploded perspective of another preferred embodiment of the present invention;

FIG. 11 is an assembled perspective of another preferred embodiment of the present invention.

DETAILED DESCRIPTION OF THE PREFERRED EMBODIMENTS

Figure 1:
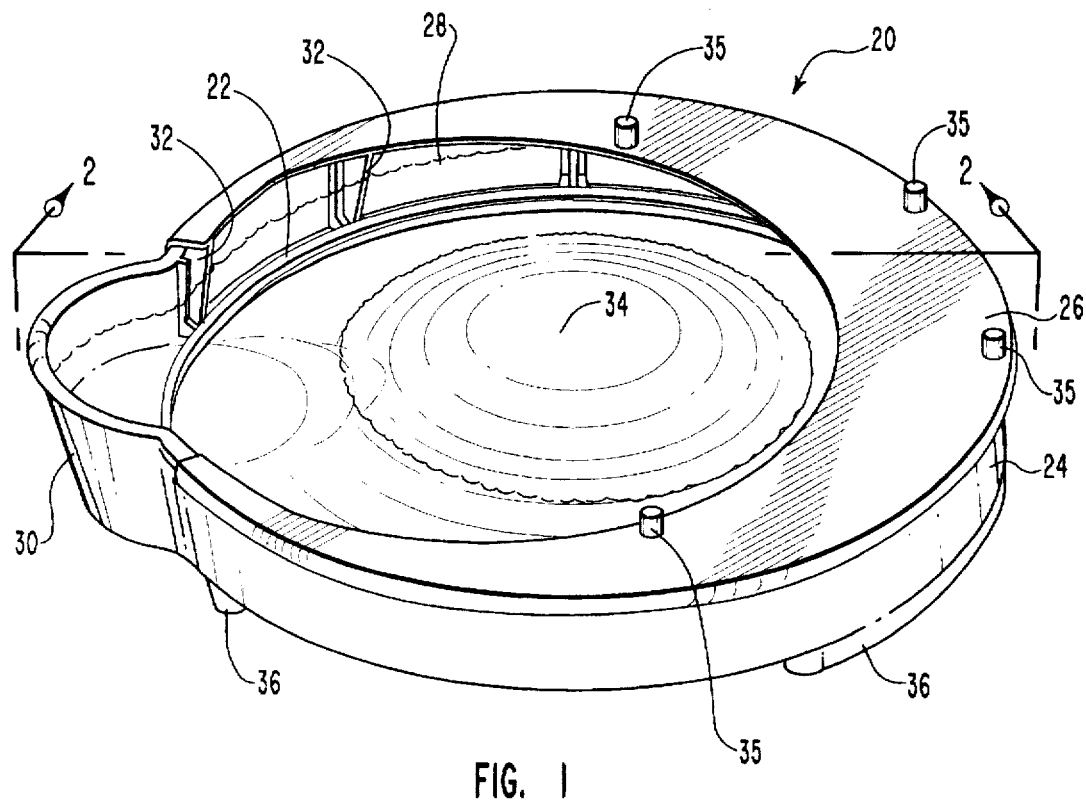
FIG. 1 is a perspective view of one preferred embodiment of the present invention.

Referring first to FIG. 1, a perspective view of one preferred embodiment of the inventive guidewire holder is presented. In FIG. 1, the guidewire holder, shown generally as 20, comprises housing means for defining a chamber which retains one or more coiled guidewires 22. By way of example, in FIG. 1 the housing means comprises pan 24 and partially enclosed cover 26. Pan 24 is preferably circular or ovoid in shape, but any shape which retains a coiled guidewire can be used.

As illustrated in FIG. 1, cover 26 has formed therein access hole 28. Access hole 28 is preferably large enough to pass coiled guidewire 22 but yet not so large that it allows coiled guidewire 22 to spring out of the guidewire holder should the guidewire work its way up the sides of pan 24. In some preferred embodiments, it may be desirable to size access hole 28 so as to minimize the amount of storage fluid which may be spilled if guidewire holder 20 is accidentally jostled. In all cases, however, access hole 28 should still be large enough to pass coiled guidewire 22.

In the embodiment illustrated in FIG. 1, access means for providing access to the one or more coiled guidewires may also be provided. By way of example, and not limitation, in FIG. 1 such access means comprises nose portion 30. The primary function of any access means included within the present invention is to allow a healthcare professional to easily grasp coiled guidewire 22 stored within guidewire holder 20. Nose portion 30 performs this function by providing an area where coiled guidewire 22 is suspended and does not touch at least the outer periphery of pan 24. In one preferred embodiment, nose portion 30 also suspends guidewire 22 so that guidewire 22 does not contact nose portion 30 at the bottom surface of pan 24. In other words, in one preferred embodiment nose portion 30 provides an area wherein guidewire 22 does not contact the inside surface, either sides or bottom, of pan 24. It is, however, not strictly necessary to provide such wide access. In some embodiments, it is sufficient that guidewire 22 is held away from the outer periphery of pan 24. An embodiment could also be envisioned where guidewire 22 was allowed to contact the outer periphery of pan 24 yet was held away from the bottom surface of pan 24. Embodiments within the scope of this invention may also provide retaining means for retaining one or more coiled guidewires substantially immersed in the storage fluid retained by the housing means. For example, in FIG. 1. such retaining means comprises a plurality of ribs 32. Ribs 32 are preferably tapered to present an inward canted surface. The inward canted surface provides an area where coiled guidewire 22 can reside. Because guidewires which are coiled have a natural tendency to spring open, by presenting an inward canted surface to the coiled guidewire the spring force of the guidewire tends to force the guidewire to travel down ribs 32 and into guidewire holder 20 so as to reside along the bottom portion of guidewire holder 20. This forces guidewire 22 further into the storage fluid and helps to prevent guidewire 22 from working its way out of guidewire holder 20 prior to removal by the healthcare professional.

Although the retaining means for retaining one or more coiled guidewires is implemented in the embodiment illustrated in FIG. 1 by ribs 32, other structures may also be used to implement this means. For example, pan 24 may be formed with inward canting sides. Such a structure would also tend to force guidewire 22 into guidewire holder 20 and prevent guidewire 22 from working its way out of guidewire holder 20. Other equivalent structures may also be used.

As previously described, guidewires are generally stored in a storage fluid such as a heparin solution. In order to reduce the amount of storage fluid required to fill guidewire holder 20, embodiments within the scope of this invention may have domed bottom 34. As illustrated in FIG. 1, domed bottom 34 decreases the volume within pan 24. Furthermore, domed bottom 34 tends to channel the storage solution to the outer periphery of pan 24 where guidewires stored therein tend to reside.

The embodiment illustrated in FIG. 1 may also comprise means for interlocking the guidewire holder to other such guidewire holders so that the guidewire holders can be stacked. In FIG. 1 such means comprises posts 35 and leg pads 36. Operation of posts 35 and leg pads 36 in interconnecting multiple guidewire holders is explained more fully hereafter. Stacking the guidewire holders is beneficial because it reduces the amount of space they occupy.

Figure 2:
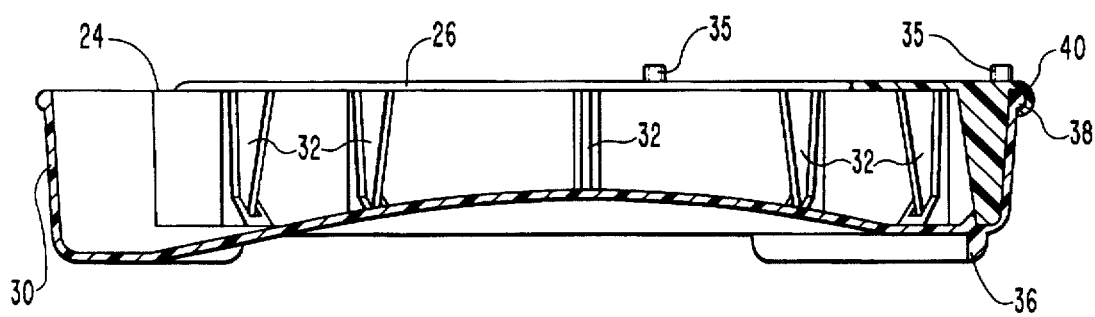
FIG. 2 is a cross section taken along the line 2—2 of FIG. 1.
Figure 4:
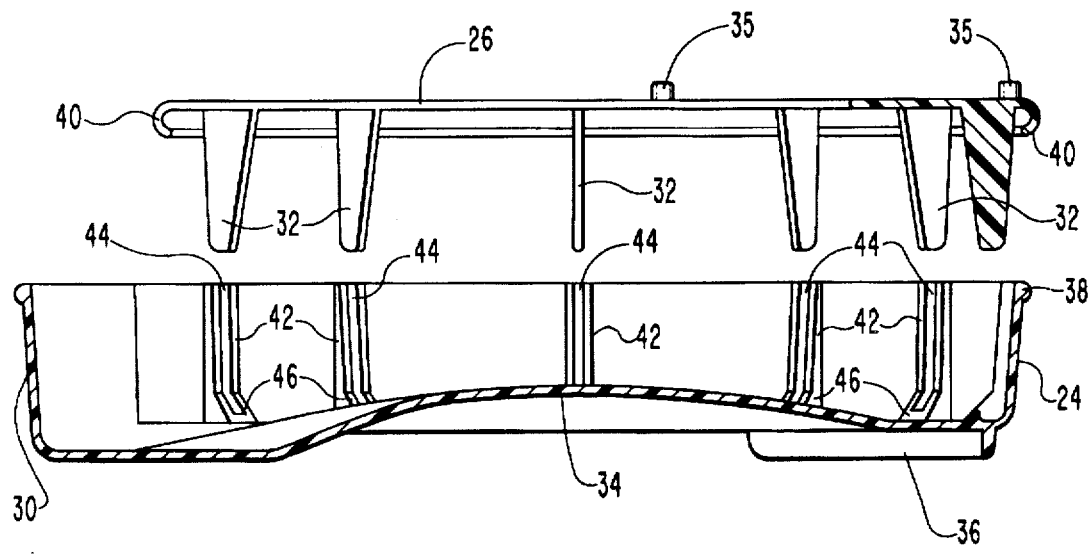
FIG. 4 is a cross section taken along the line 4—4 of FIG. 3.
Figure 5:
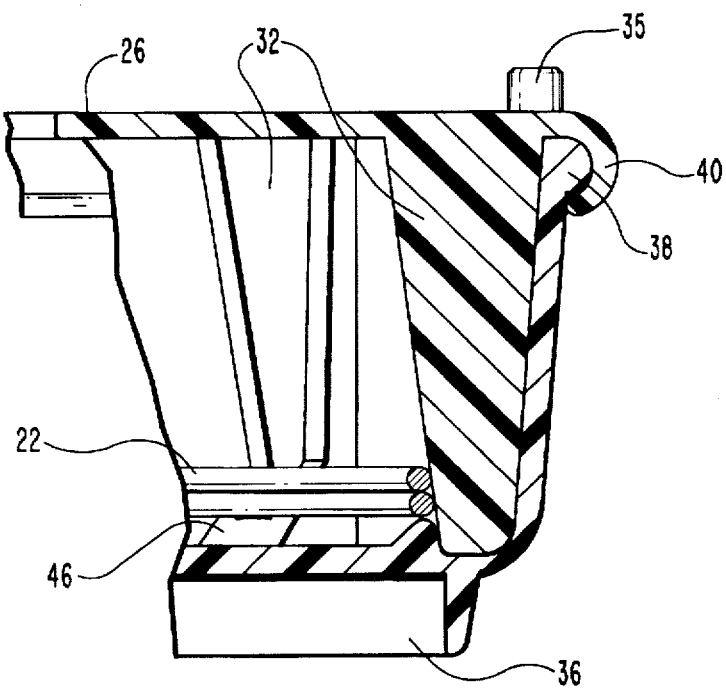
FIG. 5 is an enlarged cross section view of a portion of the preferred embodiment shown in FIGS. 1–4.

Referring next to FIGS. 2 and 5, details of one preferred embodiment are presented in cross-section. As illustrated in FIGS. 2 and 5, ribs 32 are preferably formed integral with cover 26. Guidewire holder 20 is preferably formed from an injection molding process although many different processes may be utilized. When ribs 32 are formed integral with cover 26, however, a greatly simplified molding process may be used. As previously mentioned, embodiments within the scope of this invention may comprise retaining means for retaining one or more coiled guidewires substantially immersed in the storage fluid. Also as previously indicated, in the embodiment illustrated in FIGS. 1–5, such means comprises ribs 32. By utilizing ribs 32 as part of the means for retaining one or more coiled guidewires substantially immersed in the storage fluid, the sides of pan 24 may be molded with a vertical or, perhaps, a slightly outward draft. Ribs 32 can then form an inward canted surface which helps to force guidewire 22 down into the storage fluid. Also as previously mentioned, in the absence of ribs 32, the sides of pan 24 may also be formed with a negative draft so as to present an inward canted surface to guidewire 22. However, such a structure would greatly increase the difficulty in forming pan 24 using a molding process.

In order to retain cover 26 on pan 24, coupling means for coupling cover 26 to pan 24 may also be provided. In FIGS. 2 and 5, such coupling means comprises bead 38 and lip 40. These structures are perhaps best illustrated in FIG. 5. As illustrated therein, pan 24 has formed around the upper rim bead 38. Bead 38 is designed to be received within lip 40 which is formed around the outer edge of cover 26. By forming either cover 26 alone or cover 26 and pan 24 from a moderately flexible plastic material, it can be seen that bead 38 and lip 40 will create a tight seal whereby pan 24 and cover 26 are coupled together. At the same time, such an arrangement allows pan 24 and cover 26 to be separated for cleaning, inspection, or other purposes.

Figure 3:
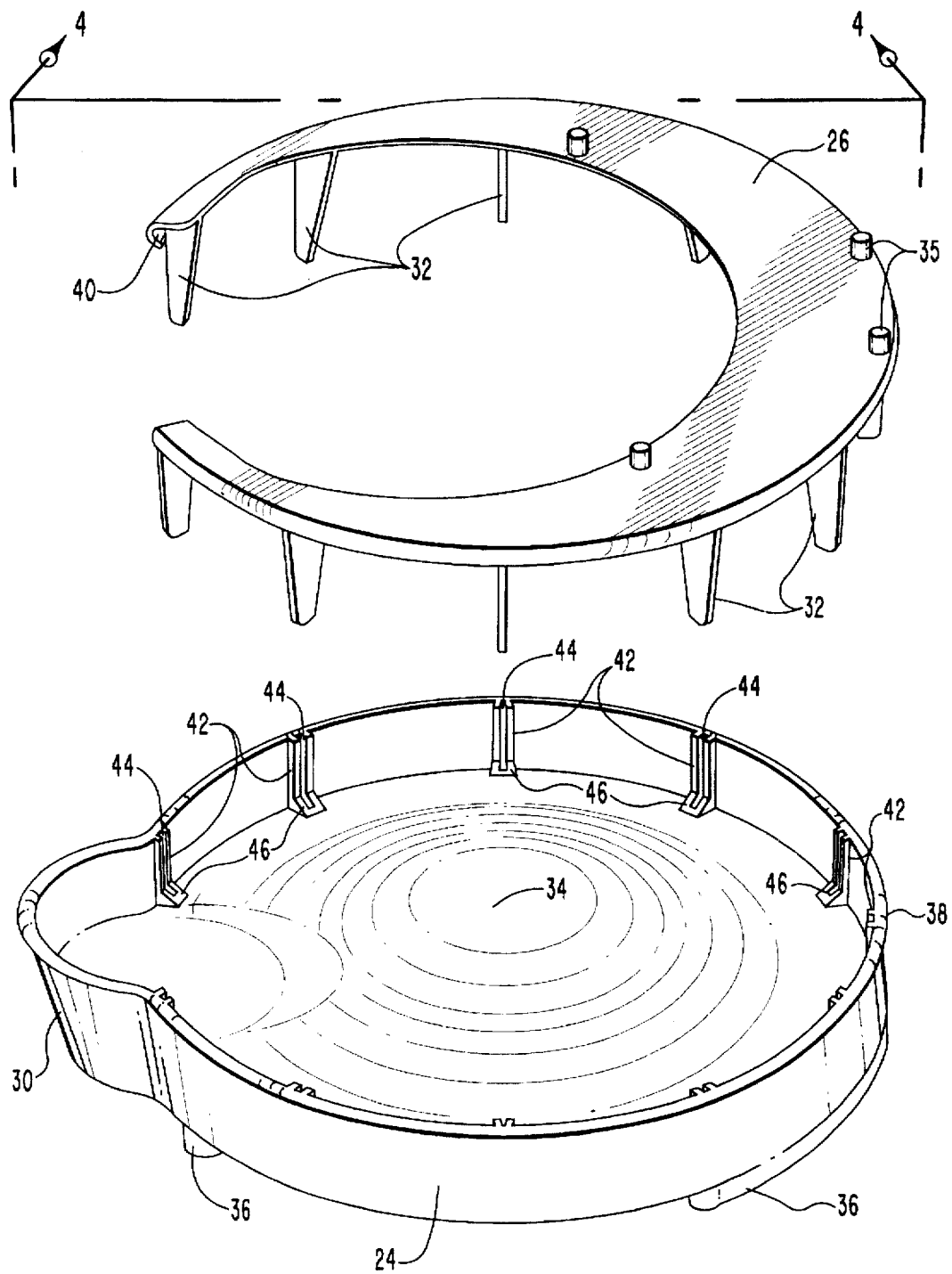
FIG. 3 is an exploded perspective of one preferred embodiment of the present invention.

Referring now to FIGS. 3 and 4, an exploded view of guidewire holder 20 is presented. As illustrated in these figures, pan 24 has formed therein a plurality of rib guides 42. Rib guides 42 have formed therein channel 44 which is designed to receive ribs 32. The purpose of rib guides 42 is to hold and stiffen ribs 32. Thus, channel 44 is preferably sized to closely receive ribs 32.

Rib guides 42 also have an integrally formed angle portion 46. Angle portion 46 is designed to combine with the inward cant of ribs 32 in order to create a V-shaped structure to retain the coiled guidewires within guidewire holder 20 and to keep coiled guidewire 22 off of the bottom of pan 24. This function is perhaps best illustrated in FIG. 5 which illustrates guidewire 22 resting at the intersection of ribs 32 and angled portion 46. By providing such a structure, guidewire 22 is held off of the bottom of pan 24 which makes guidewire 22 easier to grasp and remove from guidewire holder 20. Also as illustrated in FIGS. 2 and 4, nose portion 30 is preferably formed so that the bottom portion is lower than the V-intersection of angled portion 46 and ribs 32. This also allows guidewire 22 to rest above the bottom of the pan. Such a structure may be used to implement the access means previously described.

As also illustrated in FIG. 5, rib 32 extends behind angled portion 46 so as to be slightly below the bottom of pan 24. Although not strictly necessary, such a structure ensures that rib 32 will not create a gap between angled portion 46 and the bottom of rib 32 such that guidewire 22 can be entangled therein.

Figure 6:
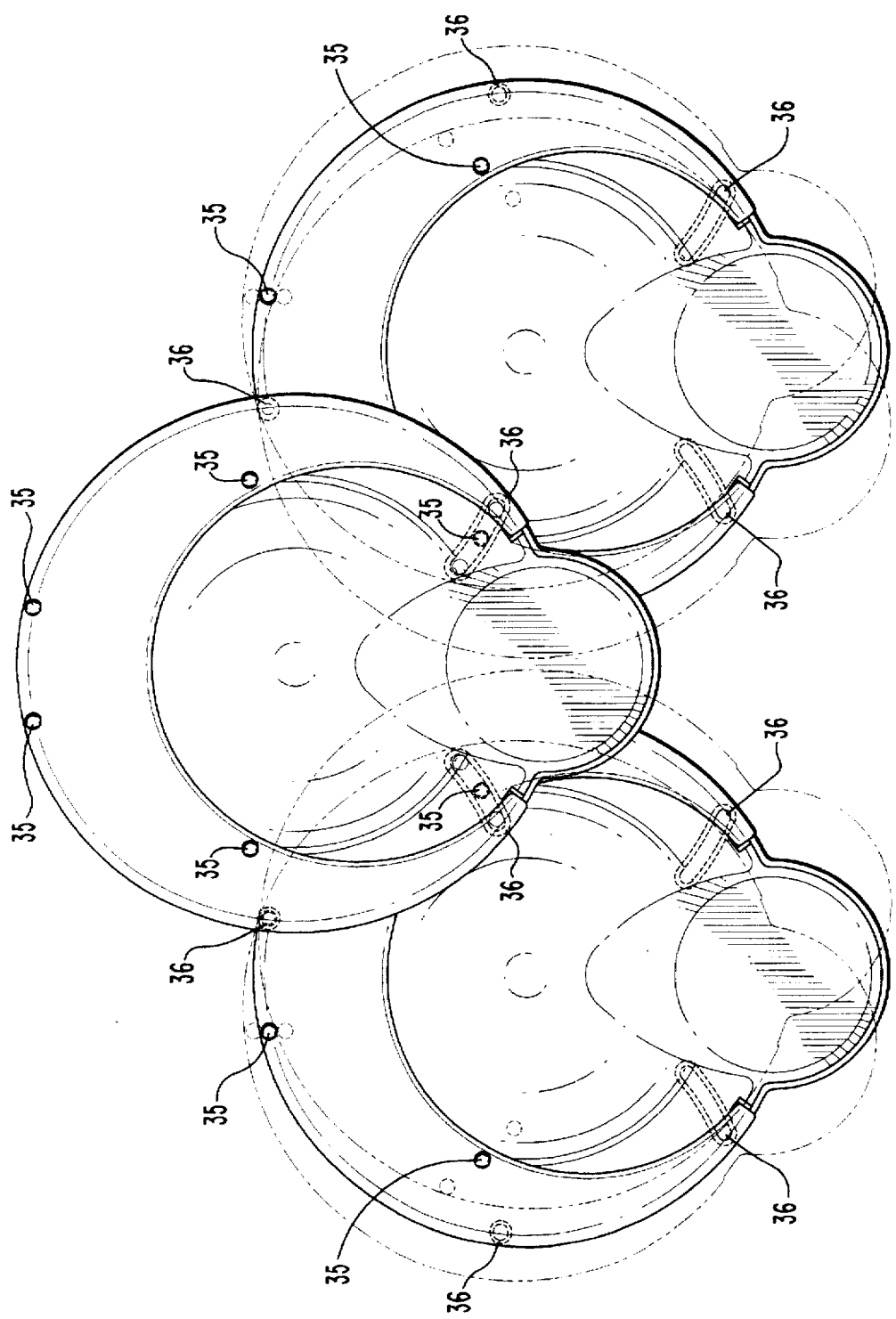
FIG. 6 is a plan view showing interconnection of a plurality of guidewire holders.

As previously mentioned, embodiments within the scope of this invention can comprise means for interlocking the guidewire holder to other such guidewire holders so that the guidewire holders can be stacked. In the embodiment illustrated in FIGS. 1–5, such means comprises posts 35 and leg pads 36. Turning now to FIG. 6, a plan view of the way in which posts 35 and leg pads 36 allow a plurality of guidewire holders to be interlocked and stacked is presented. As illustrated in FIG. 6, leg pads 36 are preferably hollow and sized to receive posts 35. In one preferred embodiment, posts 35 are located on top of cover 26 to allow engagement of leg pads 36.

As illustrated in FIG. 6, the rear leg pads are sized to receive a post 35 in a close fitting arrangement. Front leg pads 36, however, are elongated and have formed therein a hollow channel also sized to receive post 35 in a close fitting arrangement. If such an arrangement is used, then the bottom wire pans may be pivoted about the rear leg pad so that post 35 slides back and forth in the channel formed within front leg pads 36. This allows the lower guidewire holders to be rotated slightly inward or outward with respect to the top guidewire holder. Such a feature allows either greater or less access to the lower guidewire holders and may make removing guidewires from the lower guidewire holders easier. The back and forth rotation around the rear leg pad is illustrated in FIG. 6 in phantom lines.

The above structure solves a problem which must be considered when determining which structures will be used to implement the means for interlocking the guidewire holder to other such guidewire holders so that the guidewire holders can be stacked. If the selected means covers or obscures the access means which allows access to the coiled guidewires stored within the guidewire holders, then the effectiveness of the guidewire holders is reduced if they are stacked during a medical procedure. In other words, it is preferable that when means for interlocking the guidewire holder to other such guidewire holders included, such means should be selected and located so that the stacked guidewire holders still allow full access to the coiled guidewires stored therein via the access means. By selecting a structure which allows the bottom guidewire holders to be pivoted or rotated to some extent relative to the top guidewire holders, it may be possible to ensure that the access means remains unobstructed so that the coiled guidewires stored within the bottom guidewire holders can be easily removed.

Figure 7:
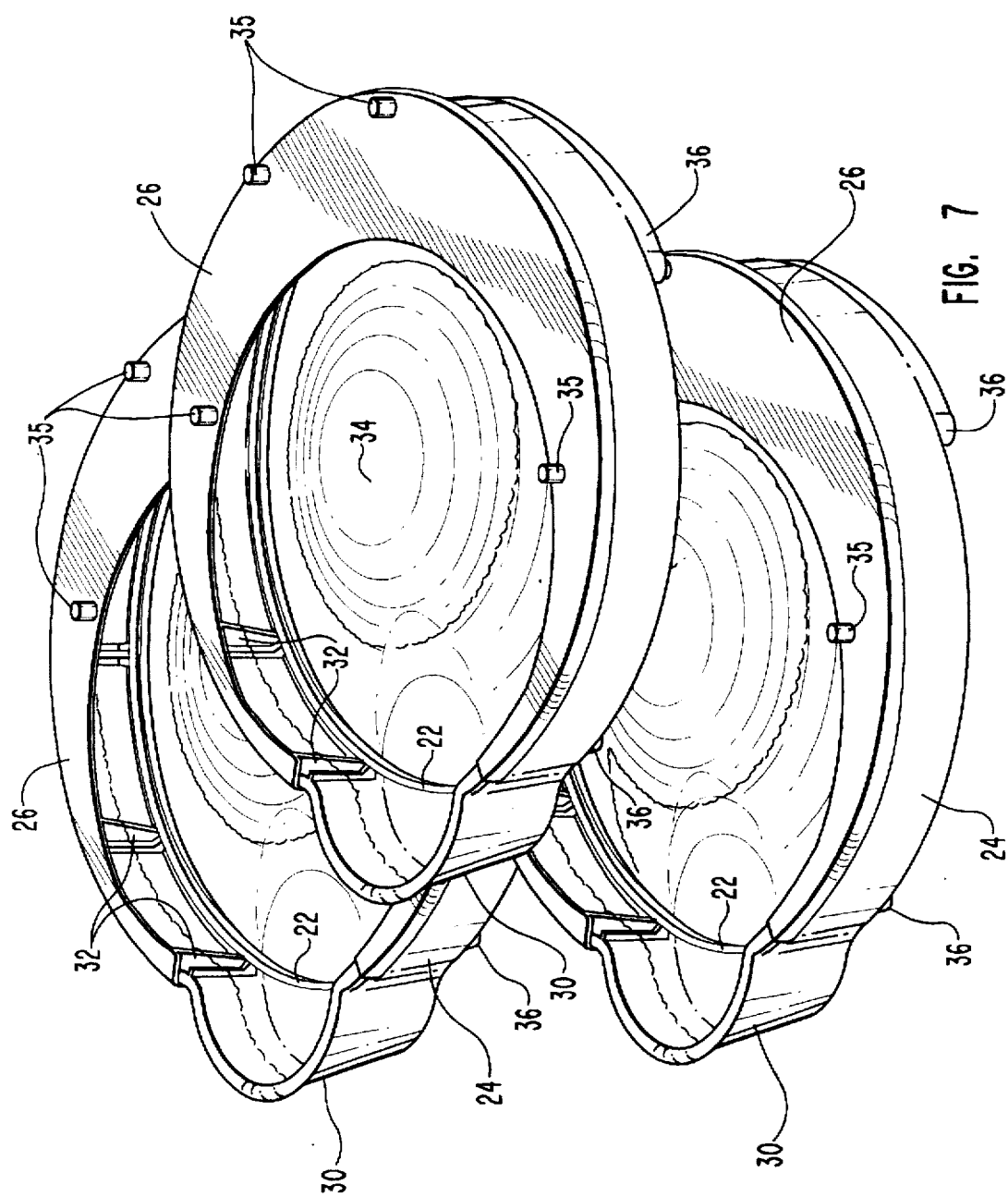
FIG. 7 is a perspective view showing interconnection of a plurality of guidewire holders.

Referring next to FIG. 7, a perspective view of three guidewire holders stacked using posts 35 and leg pads 36 to implement the means for interlocking the guidewire holder to other such guidewire holders. As illustrated therein, it is apparent that this type of structure meets the preferred criteria which is to provide unobstructed access to the coiled guidewires stored in the lower guidewire holders via the access means. Furthermore, being able to rotate the lower guidewire holders to some event with respect to the upper guidewire holder ensures that access to the lower guidewire holders is not obstructed.

Of course posts 35 and leg pads 36 as illustrated in FIGS. 6 and 7 are only illustrative and should not be construed as limiting the scope of this invention. Any means for interlocking the guidewire holder to other such guidewire holders so that the guidewire holders can be stacked may be implemented via a wide variety of structures which allow the guidewire holders to be stacked in a wide variety of orientations.

Figure 8:
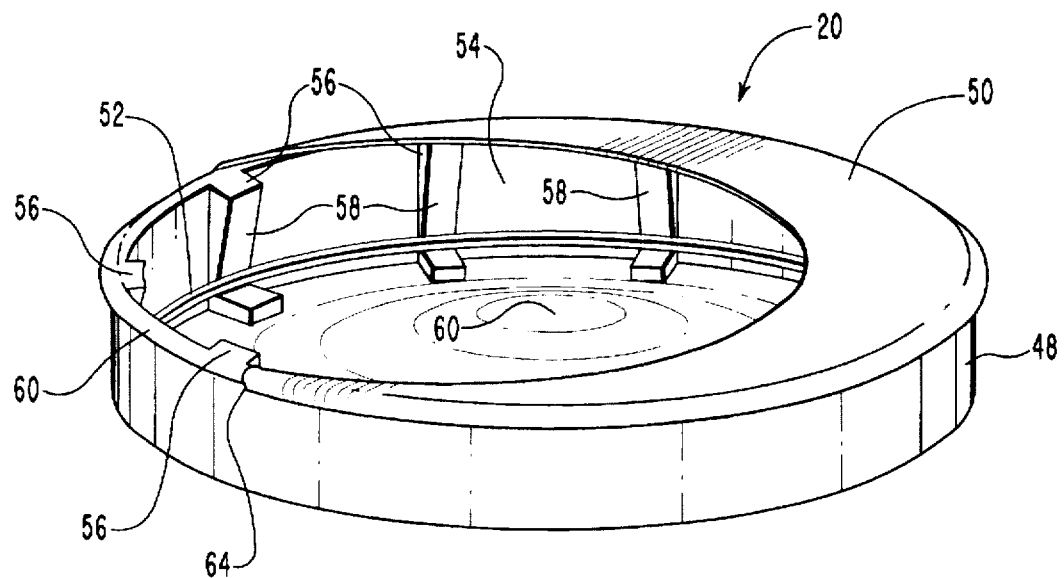
FIG. 8 is a perspective view of another preferred embodiment of the present invention.

Turning next to FIG. 8, another embodiment of the present invention is presented. As previously presented, embodiments within the scope of this invention comprise housing means for defining a chamber which retains one or more coiled guidewires. For example, in FIG. 8 such housing means comprises pan 48 and cover 50. As illustrated in FIG. 8, pan 48 and cover 50 are sized and shaped so as to retain coiled guidewire 52 therein.

Cover 50 has formed therein access hole 54. As previously described, access hole 54 should be large enough to allow guidewire 52 to pass therethrough. Also, access hole 54 should not be so large as to allow guidewire 52 to escape the guidewire holder should guidewire 52 somehow work its way to the top portion of pan 48.

The embodiment illustrated in FIG. 8 also comprises access means for providing access to the one or more coiled guidewires. In FIG. 8, such access means comprises ribs 56. As illustrated in FIG. 8, ribs 56 are shaped so as to hold guidewire 52 away from both the bottom of pan 48 and the sides of pan 48. By creating a space around guidewire 52, it is easy for a healthcare professional to reach into the guidewire holder and grasp coiled guidewire 52 in order to remove it from the guidewire holder.

The embodiment in FIG. 8 also can comprise retaining means for retaining one or more coiled guidewires substantially immersed in the storage fluid. In the embodiment illustrated in FIG. 8, such a means can comprise, for example, angled surface 58 of ribs 56. By providing ribs 56 with angled surface 58, a surface with an inward cant is presented to guidewire 52. As previously described, when a coiled guidewire is presented with a surface which is canted inwardly, the canted surface tends to force guidewire 52 down toward the bottom of pan 48. This retains guidewire 52 substantially immersed in the storage fluid.

As in previous embodiments, in order to reduce the amount of storage fluid required to cover guidewire 52, pan 48 may be provided with domed bottom 60. Domed bottom 60 reduces the volume of pan 48 and hence reduces the amount of storage fluid needed to fill pan 48. Furthermore, domed bottom 60 helps to channel the storage fluid toward the edges of pan 48 where guidewire 52 resides.

The embodiment illustrated in FIG. 8 may also comprise coupling means to couple cover 50 to pan 48. As in previous embodiments, such coupling means can comprise bead 62 formed around the rim of pan 48 and lip 64 formed around the outer edge of cover 50.

Figure 9:
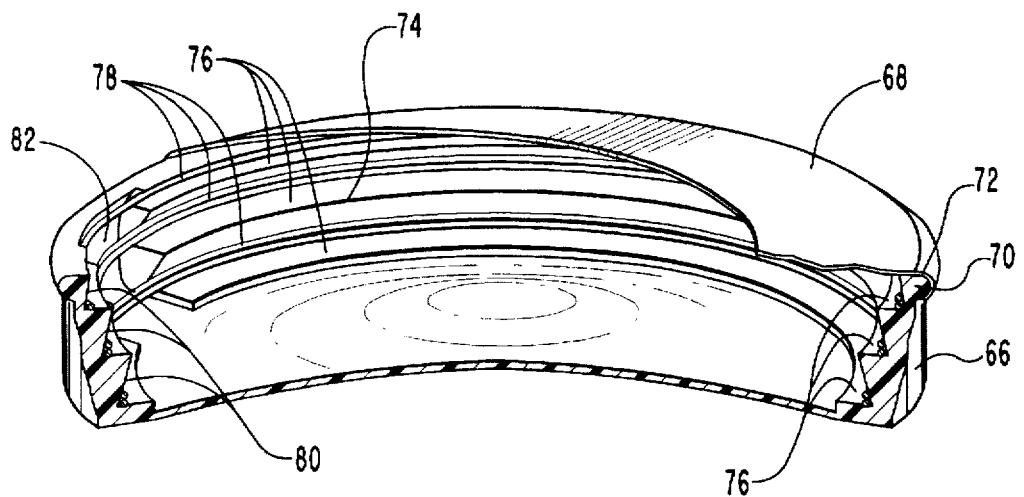
FIG. 9 is a cut-away perspective of another preferred embodiment of the present invention.

Referring next to FIG. 9, an embodiment specifically designed to store a plurality of guidewires is presented. Although any embodiments presented within this invention may hold one or more guidewires, it may be desirable to form a guidewire holder specifically to hold a plurality of guidewires.

The embodiment illustrated in FIG. 9 comprises housing means for defining a chamber which retains one or more coiled guidewires. In FIG. 9, such housing means comprises, for example, pan 66 and cover 68. As with previous embodiments presented in this invention, if pan 66 and cover 68 are formed separately, the embodiment can comprise coupling means which couples pan 66 and cover 68 together. In FIG. 9, such coupling means comprises, for example, bead 70 which is formed around the rim of pan 66 and lip 72 formed around the outer edge of cover 68.

The embodiment illustrated in FIG. 9 also comprises retaining means for retaining one or more coiled guidewires substantially immersed in the storage fluid. In FIG. 9, such retaining means can comprise, for example, shelf structure 74. Shelf structure 74 comprises a plurality of shelves 76 upon which coiled guidewires 78 rest. The plurality of shelves provides vertical separation between the plurality of guidewires. This allows a healthcare professional to locate the appropriate guidewire by feeling the vertical separation.

As illustrated in FIG. 9, shelves 76 may be separated by inclined portions 80. Inclined portions 80 will tend to force guidewires 78 so that they rest on top of shelves 76. Such a structure helps to prevent guidewires 78 from working their way out of the guidewire holder.

Although shelf structure 74 has been shown as formed integrally with pan 66, shelf structure 74 could also be formed as rib type structures either formed integrally with pan 66 or formed integrally with cover 68.

The embodiment illustrated in FIG. 9 also comprises access means for providing access to the one or more coiled guidewires. In FIG. 9, access means can comprise, for example, open area 82. As illustrated in FIG. 9, open area 82 provides a region where guidewire 78 are held away from both the sides and bottom of pan 66. This allows a healthcare professional to more easily grasp guidewire 78 in order to remove them from the guidewire holder. The vertical separation between guidewire 78 also helps a healthcare professional be able to select and grasp the appropriate guidewire.

Referring next to FIGS. 10 and 11, yet another embodiment designed to hold a plurality of guidewires is presented. The embodiment presented in FIGS. 10 and 11 comprises housing means for defining a chamber which retains one or more coiled guidewires. The embodiments illustrated in FIGS. 10 and 11, such housing means can comprise, for example, pan 84 and cover 86. The embodiment illustrated in FIGS. 10 and 11 can also comprise coupling means in order to couple pan 84 to cover 86. In FIGS. 10 and 11 such coupling means can comprise, for example, bead 88 formed around the rim of pan 84 and lip 90 formed around the outer edge of cover 86. As previously described, the bead and lip structure allows cover 86 to be removably coupled with pan 84.

The embodiment illustrated in FIGS. 10 and 11 also comprises means for retaining one or more coiled guidewires substantially immersed in the storage fluid. By way of example, and not limitation, in FIGS. 10 and 11 such means comprises shelf structure 92. As perhaps best illustrated in FIG. 210, shelf structure 92 is formed integrally with cover Shelf structure 92 comprises vertical member 94 and a plurality of shelves 96 extending from vertical member 94. Shelves 96 are separated by a vertical distance so that a plurality of guidewires 98 can rest thereon with sufficient separation to allow a healthcare professional to differentiate between various guidewires by their vertical separation.

Although shelf structure 92 is illustrated in FIGS. 10 and 111 as comprising vertical member 94, it would also be possible to form shelf structure 92 with vertical member 94 oriented at an inward cant. This would provide not only vertical separation but also provide a horizontal separation between guidewires 98 as well.

The embodiments illustrated in FIGS. 10 and 11 also comprise access means for providing access to the one or more coiled guidewires. In FIGS. 10 and 11, such access means can comprise, for example, nose portion 100. Nose portion 100 provides a region wherein guidewires 98 are held away from the edge portion of pan 84. Such a separation allows the healthcare professional to be able to grasp the desired guidewire and remove it from the guidewire holder.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A guidewire holder for storage and retrieval of at least one coiled guidewire, the guidewire holder comprising:
   a) housing means for defining a partially covered chamber which is adapted to retain at least one guidewire substantially immersed in a storage fluid, the housing means comprising a pan means for defining a bottom portion with an outer periphery of the housing means, and a cover means for defining a separate top portion of the housing means;
   b) said pan means comprising channel means for holding a sufficient quantity of the storage fluid therein to permit the at least one guidewire to be immersed therein, and said pan means further comprising means for retaining the at least one guidewire immersed in the storage fluid by suspending the at least one guidewire so that it does not contact the outer periphery of said bottom portion; and
   c) said pan means and said cover means together defining:
      first access means defining a first access opening in said cover means which is large enough to permit a coiled guidewire to be easily inserted and withdrawn therethrough, but said first access opening being small enough so that said cover means substantially covers the channel means in which the storage fluid is held and in which the guidewire is retained; and second access means in the form of an offset nose portion defined is said pan means for facilitating grasping the guidewire by hand for removal from said channel means.

2. A guidewire holder as recited in claim 1 wherein the housing means has a side which is canted inward.

3. A guidewire holder as recited in claim 1 wherein the offset nose portion is formed so that the at least one coiled guidewire does not touch the housing means at said nose portion.

4. A guidewire holder as recited in claim 1 wherein said housing means has an inside surface and the access means comprises means to hold the at least one coiled guidewire away from the inside surface of the housing means.

5. A guidewire holder as recited in claim 4 wherein the means to hold the at least one guidewire away from the inside surface of the housing means comprises at least one rib.

6. A guidewire holder as recited in claim 1 further comprising a plurality of ribs attached to the cover, extending downward into the housing means along the inside surface of the housing means.

7. A guidewire holder as recited in claim 1 wherein the housing means has a substantially circular shape.

8. A guidewire holder as recited in claim 1 further comprising means for interlocking the guidewire holder to other such guidewire holders so that the guidewire holders can be stacked.

9. A stackable system of guidewire holders for storage and retrieval of a plurality of guidewires each separately held by one of the guidewire holders, each guidewire holder comprising:
   a) housing means for defining a partially covered chamber which is adapted to retain at least one guidewire substantially immersed in a storage fluid, the housing means comprising a pan means for defining a bottom portion with an outer periphery of the housing means, and a cover means for defining a top portion of the housing means;
   b) said pan means comprising channel means for holding a sufficient quantity of the storage fluid therein to permit the at least one guidewire to be immersed therein, and said pan means further comprising means for retaining the at least one guidewire immersed in the storage fluid by suspending the guidewire so that it does not contact the outer periphery of said bottom portion;

c) said pan means and said cover means together defining:
first access means defining a first access opening in said cover means which is large enough to permit a coiled guidewire to be easily inserted and withdrawn therethrough, but said first access opening being small enough so that said cover means substantially covers the channel means in which the storage fluid is held and in which the guidewire is retained; and
second access means in the form of an offset nose means defined in said pan means for forming a second access opening which facilitates grasping the guidewire by hand for removal from said channel means and through said first access opening; and d) means for stacking at least one of said guidewire holders on top of another guidewire holder, but without substantially obscuring either of said first and second access means.

10. A guidewire holder as recited in claim 9 wherein the retaining means comprises at least one rib disposed along the inside surface of the housing means.

11. A guidewire holder as recited in claim 10 wherein the at least one rib is tapered to present an inward canted surface to the at least one guidewire.

12. A guidewire holder as recited in claim 11 wherein the housing means has a substantially circular shape.

13. A guidewire holder as recited in claim 12 wherein the offset nose portion suspends at least a portion of the at least one coiled guidewire so that said suspended portion does not contact the inside surface of the housing means.

14. A guidewire holder as recited in claim 13 wherein the nose portion of the housing means has a substantially circular shape with a diameter smaller than the diameter of the remainder of the housing means.

15. A guidewire holder as recited in claim 14 wherein the housing means has a domed bottom which reduces the amount of storage fluid needed to cover the at least one coiled guidewire.

16. A guidewire holder for storage and retrieval of at least one coiled guidewire, the guidewire holder comprising:

a) housing means for defining a partially covered chamber which is adapted to retain at least one guidewire substantially immersed in a storage fluid, the housing means comprising a pan means for defining a bottom portion with an outer periphery of the housing means, and a cover means for defining a separate top portion of the housing means, and said pan means and said cover means together defining means for releasable connection of the cover means onto the pan means to permit assembly and disassembly thereof;

b) said pan means comprising channel means for holding a sufficient quantity of the storage fluid therein to permit the at least one guidewire to be immersed therein, and said pan means further comprising means for retaining the at least one guidewire immersed in the storage fluid by suspending the at least one guidewire so that it does not contact the outer periphery of said bottom portion; and c) said pan means and said cover means together defining:
first access means defining a first access opening in said cover means which is large enough to permit a coiled guidewire to be easily inserted and withdrawn therethrough, but said first access opening being small enough so that said cover means substantially covers the channel means in which the storage fluid is held and in which the guidewire is retained; and
second access means in the form of an offset nose means defined in said pan means for forming a second access opening which facilitates grasping the guidewire by hand for removal from said channel means and through said first access opening.

17. A guidewire holder as recited in claim 16 wherein the nose portion of the housing means is formed so that said nose portion does not contact the at least one guidewire.

* * * * *

UNITED STATES PATENT AND TRADEMARK OFFICE
CERTIFICATE OF CORRECTION

PATENT NO. : 5,738,213
DATED : April 14, 1998
INVENTOR(S) : John Whiting et al.

It is certified that error appears in the above-identified patent and that said Letters Patent is hereby corrected as shown below:

Col. 1, line 31, delete "anglographic" and replace with --angiographic--

Col. 2, line 19, after "open and" delete "to"

Col. 4, line 6, delete "park" and replace with --pan--

Col. 7, line 53, delete "event" and replace with --extent--

Col. 9, line 13, delete "are" and replace with --is--

Col. 9, line 39, delete "210" and replace with --10--

Col. 9, line 41, after "cover" add --86.--

Signed and Sealed this

Twenty-fourth Day of August, 1999

Attest:

Q. TODD DICKINSON

*Attesting Officer*     Acting Commissioner of Patents and Trademarks